United States Patent
Duan et al.

(10) Patent No.: US 12,089,931 B1
(45) Date of Patent: Sep. 17, 2024

(54) OPTICAL SENSOR FOR SKIN-CONTACT DETECTION AND PHYSIOLOGICAL PARAMETER MEASUREMENT AT WEARABLE ELECTRONIC DEVICE

(71) Applicant: Apple Inc., Cupertino, CA (US)

(72) Inventors: Xiyu Duan, San Jose, CA (US); Albert E. Cerussi, San Jose, CA (US); Paul D. Mannheimer, Los Altos, CA (US); Saeed Mohammadi, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 314 days.

(21) Appl. No.: 17/407,843

(22) Filed: Aug. 20, 2021

Related U.S. Application Data

(60) Provisional application No. 63/077,457, filed on Sep. 11, 2020.

(51) Int. Cl.
*A61B 5/1455* (2006.01)
*A61B 5/00* (2006.01)

(52) U.S. Cl.
CPC .......... *A61B 5/14552* (2013.01); *A61B 5/681* (2013.01); *A61B 5/6844* (2013.01); *A61B 5/742* (2013.01); *A61B 2560/04* (2013.01); *A61B 2562/0238* (2013.01)

(58) Field of Classification Search
CPC ... A61B 5/14552; A61B 5/681; A61B 5/6844; A61B 5/742; A61B 2560/04; A61B 2562/0238
See application file for complete search history.

(56) References Cited

U.S. PATENT DOCUMENTS

| | | |
|---|---|---|
| 4,931,767 A | 6/1990 | Albrecht et al. |
| 5,287,376 A | 2/1994 | Paoli |
| 5,483,261 A | 1/1996 | Yasutake |
| 5,488,204 A | 1/1996 | Mead et al. |
| 5,488,678 A | 1/1996 | Taneya |
| 5,617,439 A | 4/1997 | Kakimoto |
| 5,644,667 A | 7/1997 | Tabuchi |
| 5,742,631 A | 4/1998 | Paoli |

(Continued)

FOREIGN PATENT DOCUMENTS

| | | |
|---|---|---|
| EP | 1403985 | 3/2004 |
| EP | 1432045 | 6/2004 |

(Continued)

OTHER PUBLICATIONS

US 11,819,316 B1, 11/2023, Allec et al. (withdrawn)

(Continued)

*Primary Examiner* — Eric F Winakur
*Assistant Examiner* — Abid A Mustansir
(74) *Attorney, Agent, or Firm* — Brownstein Hyatt Farber & Schreck, LLP

(57) ABSTRACT

A wearable electronic device (e.g., an electronic watch) may detect and analyze one or more sensing signals corresponding to light detected by the device to determine whether the device is in a sensing state (e.g., the device is within a maximum sensing distance of a user). If the wearable electronic device is in the sensing state, the device may determine one or more physiological parameters from the same signals used to determine whether the device is in the sensing state.

20 Claims, 12 Drawing Sheets

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,848,088 A | 12/1998 | Mori et al. |
| 5,880,411 A | 3/1999 | Gillespie et al. |
| 5,940,556 A | 8/1999 | Moslehi et al. |
| 6,083,172 A | 7/2000 | Baker, Jr. et al. |
| 6,094,270 A | 7/2000 | Uomori |
| 6,122,042 A | 9/2000 | Wunderman et al. |
| 6,188,391 B1 | 2/2001 | Seely et al. |
| 6,310,610 B1 | 10/2001 | Beaton et al. |
| 6,330,378 B1 | 12/2001 | Forrest |
| 6,345,133 B1 | 2/2002 | Morozov |
| 6,393,185 B1 | 5/2002 | Deacon |
| 6,526,300 B1 | 2/2003 | Kiani et al. |
| 6,533,729 B1 | 3/2003 | Khair |
| 6,584,136 B2 | 6/2003 | Ju et al. |
| 6,594,409 B2 | 7/2003 | Dutt et al. |
| 6,615,065 B1 | 9/2003 | Barrett et al. |
| 6,628,686 B1 | 9/2003 | Sargent |
| 6,657,723 B2 | 12/2003 | Cohen |
| 6,662,033 B2 | 12/2003 | Casciani et al. |
| 6,690,387 B2 | 2/2004 | Zimmerman et al. |
| 6,795,622 B2 | 9/2004 | Forrest |
| 6,892,449 B1 | 5/2005 | Brophy et al. |
| 6,940,182 B2 | 9/2005 | Hilton et al. |
| 6,947,639 B2 | 9/2005 | Singh |
| 6,952,504 B2 | 10/2005 | Bi |
| 6,987,906 B2 | 1/2006 | Nakama et al. |
| 7,015,894 B2 | 3/2006 | Morohoshi |
| 7,054,517 B2 | 5/2006 | Mossberg |
| 7,058,245 B2 | 6/2006 | Farahi |
| 7,079,715 B2 | 7/2006 | Kish |
| 7,184,064 B2 | 2/2007 | Zimmerman et al. |
| 7,203,401 B2 | 4/2007 | Mossberg |
| 7,203,426 B2 | 4/2007 | Wu et al. |
| 7,209,611 B2 | 4/2007 | Joyner |
| 7,237,858 B2 | 7/2007 | Igarashi |
| 7,245,379 B2 | 7/2007 | Schwabe |
| 7,269,356 B2 | 9/2007 | Winzer |
| 7,283,694 B2 | 10/2007 | Welch |
| 7,314,451 B2 | 1/2008 | Halperin et al. |
| 7,324,195 B2 | 1/2008 | Packirisamy et al. |
| 7,366,364 B2 | 4/2008 | Singh |
| 7,444,048 B2 | 10/2008 | Peters et al. |
| 7,447,393 B2 | 11/2008 | Yan |
| 7,460,742 B2 | 12/2008 | Joyner |
| 7,477,384 B2 | 1/2009 | Schwabe |
| 7,483,599 B2 | 1/2009 | Dominic et al. |
| 7,526,007 B2 | 4/2009 | Chua et al. |
| 7,558,301 B2 | 7/2009 | Lin et al. |
| 7,616,110 B2 | 11/2009 | Crump et al. |
| 7,643,860 B2 | 1/2010 | Gueissaz |
| 7,663,607 B2 | 2/2010 | Hotelling et al. |
| 7,680,364 B2 | 3/2010 | Nilsson |
| 7,689,075 B2 | 3/2010 | Jenkins et al. |
| 7,720,328 B2 | 5/2010 | Yan |
| 7,798,634 B2 | 9/2010 | Miyahara et al. |
| 7,885,302 B2 | 2/2011 | Eberhard |
| 7,885,492 B2 | 2/2011 | Welch |
| 7,974,504 B2 | 7/2011 | Nagarajan |
| 8,019,400 B2 | 9/2011 | Diab et al. |
| 8,175,670 B2 | 5/2012 | Baker, Jr. et al. |
| 8,300,994 B2 | 10/2012 | Welch et al. |
| 8,378,811 B2 | 2/2013 | Crump et al. |
| 8,515,217 B2 | 8/2013 | Bernasconi et al. |
| 8,559,775 B2 | 10/2013 | Babie et al. |
| 8,564,784 B2 | 10/2013 | Wang et al. |
| 8,618,930 B2 | 12/2013 | Papadopoulos et al. |
| 8,700,111 B2 | 4/2014 | LeBoeuf et al. |
| 8,724,100 B1 | 5/2014 | Asghari et al. |
| 8,792,869 B2 | 7/2014 | Prentice et al. |
| 8,873,026 B2 | 10/2014 | Puig |
| 8,920,332 B2 | 12/2014 | Hong et al. |
| 8,948,832 B2 | 2/2015 | Hong et al. |
| 8,983,250 B2 | 3/2015 | Black et al. |
| 9,020,004 B2 | 4/2015 | Jeong |
| 9,028,123 B2 | 5/2015 | Nichol |
| 9,031,412 B2 | 5/2015 | Nagarajan |
| 9,039,614 B2 | 5/2015 | Yuen et al. |
| 9,049,998 B2 | 6/2015 | Brumback et al. |
| 9,066,691 B2 | 6/2015 | Addison et al. |
| 9,091,715 B2 | 7/2015 | Alameh et al. |
| 9,110,259 B1 | 8/2015 | Black |
| 9,135,397 B2 | 9/2015 | Denyer et al. |
| 9,176,282 B2 | 11/2015 | Pottier |
| 9,217,669 B2 | 12/2015 | Wu et al. |
| 9,237,855 B2 | 1/2016 | Hong et al. |
| 9,241,635 B2 | 1/2016 | Yuen et al. |
| 9,274,507 B2 | 3/2016 | Kim et al. |
| 9,314,197 B2 | 4/2016 | Eisen et al. |
| 9,348,154 B2 | 5/2016 | Hayakawa |
| 9,360,554 B2 | 6/2016 | Retterath et al. |
| 9,370,689 B2 | 6/2016 | Guillama et al. |
| 9,392,946 B1 | 7/2016 | Sarantos |
| 9,405,066 B2 | 8/2016 | Mahgerefteh |
| 9,423,418 B2 | 8/2016 | Alameh et al. |
| 9,510,790 B2 | 12/2016 | Kang et al. |
| 9,513,321 B2 | 12/2016 | Frangen |
| 9,515,378 B2 | 12/2016 | Prasad |
| 9,526,421 B2 | 12/2016 | Papadopoulos et al. |
| 9,526,433 B2 | 12/2016 | Lapetina et al. |
| 9,543,736 B1 | 1/2017 | Barwicz et al. |
| 9,558,336 B2 | 1/2017 | Lee |
| 9,603,569 B2 | 3/2017 | Mirov et al. |
| 9,620,931 B2 | 4/2017 | Tanaka |
| 9,643,181 B1 | 5/2017 | Chang |
| 9,766,370 B2 | 9/2017 | Aloe et al. |
| 9,784,829 B2 | 10/2017 | Zeng |
| 9,804,027 B2 | 10/2017 | Fish et al. |
| 9,829,631 B2 | 11/2017 | Lambert |
| 9,833,179 B2 | 12/2017 | Ikeda |
| 9,861,286 B1 | 1/2018 | Islam |
| 9,875,560 B2 | 1/2018 | Rajagopaian |
| 9,880,352 B2 | 1/2018 | Florjanczyk |
| 9,943,237 B2 | 4/2018 | Baker et al. |
| 9,946,020 B1 | 4/2018 | Horth |
| 9,948,063 B2 | 4/2018 | Caneau et al. |
| 9,952,433 B2 | 4/2018 | Um et al. |
| 9,974,466 B2 | 5/2018 | Kimmel |
| 10,009,668 B2 | 6/2018 | Liboiron-Ladouceur |
| 10,016,613 B2 | 7/2018 | Kavounas et al. |
| 10,132,996 B2 | 11/2018 | Lambert |
| 10,136,859 B2 | 11/2018 | Cutaia |
| 10,181,021 B2 | 1/2019 | Verkatraman et al. |
| 10,188,330 B1 | 1/2019 | Kadlec et al. |
| 10,203,454 B2 | 2/2019 | Liu |
| 10,238,351 B2 | 3/2019 | Halperin et al. |
| 10,243,684 B2 | 3/2019 | Wen |
| 10,278,591 B2 | 5/2019 | Gil |
| 10,285,898 B2 | 5/2019 | Douglas et al. |
| 10,310,196 B2 | 6/2019 | Hutchison |
| 10,317,200 B1 | 6/2019 | Han et al. |
| 10,372,160 B2 | 8/2019 | Lee et al. |
| 10,376,164 B2 | 8/2019 | Presura et al. |
| 10,429,597 B2 | 10/2019 | ten Have et al. |
| 10,444,067 B2 | 10/2019 | Hsu et al. |
| 10,529,003 B2 | 1/2020 | Mazed |
| 10,537,270 B2 | 1/2020 | Sarussi et al. |
| 10,559,708 B2 | 2/2020 | Chua |
| 10,610,157 B2 | 4/2020 | Pandya et al. |
| 10,645,470 B2 | 5/2020 | Baxi et al. |
| 10,646,145 B2 | 5/2020 | Pekander et al. |
| 10,702,211 B2 | 7/2020 | Clavelle et al. |
| 10,705,211 B2 | 7/2020 | Jacobs et al. |
| 10,741,064 B2 | 8/2020 | Schwarz et al. |
| 10,795,508 B2 | 10/2020 | Han et al. |
| 10,799,133 B2 | 10/2020 | Lee |
| 10,806,386 B2 | 10/2020 | Lobbestael et al. |
| 10,843,066 B2 | 11/2020 | Nicoli |
| 10,852,492 B1 | 12/2020 | Vermeulen et al. |
| 10,874,348 B1 | 12/2020 | Han et al. |
| 10,996,399 B2 | 5/2021 | Yang et al. |
| 11,035,318 B2 | 6/2021 | Kuboyama et al. |
| 11,145,310 B2 | 10/2021 | Sakurai |

(56) References Cited

U.S. PATENT DOCUMENTS

| | | |
|---|---|---|
| 11,156,497 B2 | 10/2021 | Bismuto et al. |
| 11,158,996 B2 | 10/2021 | Bismuto et al. |
| 11,190,556 B2 | 11/2021 | Meiyappan et al. |
| 11,224,381 B2 | 1/2022 | McHale et al. |
| 11,226,459 B2 | 1/2022 | Bishop et al. |
| 11,255,663 B2 | 2/2022 | Binder |
| 11,309,929 B2 | 4/2022 | Wong |
| 11,482,513 B2 | 10/2022 | Krasulick et al. |
| 11,511,440 B2 | 11/2022 | Polanco et al. |
| 11,857,298 B1 | 1/2024 | Allec et al. |
| 2002/0029128 A1 | 3/2002 | Jones et al. |
| 2005/0053112 A1 | 3/2005 | Shams-Zadeh-Amiri |
| 2005/0063431 A1 | 3/2005 | Gallup et al. |
| 2006/0002443 A1 | 1/2006 | Farber et al. |
| 2006/0253010 A1 | 11/2006 | Brady et al. |
| 2008/0044128 A1 | 2/2008 | Kish et al. |
| 2008/0310470 A1 | 12/2008 | Ooi et al. |
| 2010/0158067 A1 | 6/2010 | Nakatsuka et al. |
| 2012/0119920 A1 | 5/2012 | Sallop et al. |
| 2012/0310062 A1 | 12/2012 | Li et al. |
| 2013/0030267 A1 | 1/2013 | Lisogurski et al. |
| 2014/0029943 A1 | 1/2014 | Mathai et al. |
| 2014/0069951 A1 | 3/2014 | Schmidt et al. |
| 2014/0073968 A1 | 3/2014 | Engelbrecht et al. |
| 2015/0099943 A1 | 4/2015 | Russell |
| 2015/0164352 A1 | 6/2015 | Yoon et al. |
| 2016/0129279 A1 | 5/2016 | Ferolito |
| 2016/0199002 A1* | 7/2016 | Lee ............... A61B 5/0059 340/870.07 |
| 2016/0224750 A1 | 8/2016 | Kethman et al. |
| 2017/0095216 A1 | 4/2017 | Laty |
| 2017/0115825 A1 | 4/2017 | Eriksson et al. |
| 2017/0135633 A1 | 5/2017 | Connor |
| 2017/0164878 A1 | 6/2017 | Connor |
| 2017/0347902 A1 | 12/2017 | Van Gool et al. |
| 2017/0360316 A1* | 12/2017 | Gu ............... A61B 5/7475 |
| 2018/0014785 A1 | 1/2018 | Li |
| 2018/0073924 A1 | 3/2018 | Steinmann et al. |
| 2018/0098708 A1 | 4/2018 | Lee |
| 2018/0156660 A1 | 6/2018 | Turgeon et al. |
| 2018/0227754 A1 | 8/2018 | Paez Velazquez |
| 2019/0015045 A1 | 1/2019 | Li |
| 2019/0069781 A1 | 3/2019 | Kim et al. |
| 2019/0083034 A1 | 3/2019 | Shim et al. |
| 2019/0339468 A1 | 11/2019 | Evans et al. |
| 2019/0342009 A1 | 11/2019 | Evans et al. |
| 2020/0085374 A1* | 3/2020 | Lin ............... A61B 5/02438 |
| 2020/0253547 A1 | 8/2020 | Harris et al. |
| 2020/0297955 A1 | 9/2020 | Shouldice |
| 2021/0194481 A1 | 6/2021 | Rademeyer et al. |
| 2022/0011157 A1 | 1/2022 | Bismuto et al. |
| 2022/0059992 A1 | 2/2022 | Hill et al. |
| 2022/0075036 A1 | 3/2022 | Zhou et al. |
| 2022/0091333 A1 | 3/2022 | Wu |
| 2022/0099896 A1 | 3/2022 | Arbore et al. |
| 2023/0404419 A1 | 12/2023 | Allec et al. |

FOREIGN PATENT DOCUMENTS

| | | |
|---|---|---|
| EP | 3561561 | 10/2019 |
| FR | 2949024 | 2/2011 |
| JP | S60127776 | 7/1985 |
| JP | S63177495 | 7/1988 |
| JP | 2000163031 | 6/2000 |
| JP | 2002342033 | 11/2002 |
| JP | 2008262118 | 10/2008 |
| WO | WO 01/014929 | 3/2001 |
| WO | WO 02/011339 | 2/2002 |
| WO | WO 04/031824 | 4/2004 |
| WO | WO 05/091036 | 9/2005 |
| WO | WO 11/090274 | 7/2011 |
| WO | WO 15/051253 | 4/2015 |
| WO | WO 15/094378 | 6/2015 |
| WO | WO 15/105881 | 7/2015 |
| WO | WO 17/040431 | 3/2017 |
| WO | WO 17/184420 | 10/2017 |
| WO | WO 17/184423 | 10/2017 |
| WO | WO 19/152990 | 8/2019 |
| WO | WO 20/106974 | 5/2020 |

OTHER PUBLICATIONS

Gonzalez-Sanchez et al., "Capacitive Sensing for Non-Invasive Breathing and Heart Monitoring in Non-Restrained, Non-Sedated Laboratory Mice," Sensors 2016, vol. 16, No. 1052, pp. 1-16.

He et al., "Integrated Polarization Compensator for WDM Waveguide Demultiplexers," IEEE Photonics Technology Letters vol. 11, No. 2, Feb. 1999, pp. 224-226.

Kybartas et al., "Capacitive Sensor for Respiratory Monitoring," Conference "Biomedical Engineering," Nov. 2015, 6 pages.

Lapedus, "Electroplating IC Packages—Tooling challenges increase as advanced packaging ramps up," Semiconductor Engineering, https://semiengineering.com/electroplating-ic-packages, Apr. 10, 2017, 22 pages.

Materials and Processes for Electronic Applications, Series Editor: James J. Licari, AvanTeco, Whittier, California, Elsevier Inc., 2009, 20 pages.

Worhoff et al., "Flip-chip assembly for photonic circuits," MESA+ Research Institute, University of Twente, Integrated Optical MicroSystems Group, The Netherlands, 2004, 12 pages.

* cited by examiner

OPTICAL SENSOR FOR SKIN-CONTACT DETECTION AND PHYSIOLOGICAL PARAMETER MEASUREMENT AT WEARABLE ELECTRONIC DEVICE

CROSS-REFERENCE TO RELATED APPLICATION

This application is a nonprovisional of and claims the benefit under 35 U.S.C. 119(e) of U.S. Provisional Patent Application No. 63/077,457, filed Sep. 11, 2020, the contents of which are incorporated herein by reference as if fully disclosed herein.

FIELD

Embodiments relate generally to determining whether electronic devices are in a sensing state to measure physiological parameters. More particularly, the described embodiments relate to methods and systems for detecting and analyzing one or more sensing signals corresponding to light detected by the device to determine whether the device is in a sensing state, and using the sensing signals to determine physiological parameters if the device is in the sensing state.

BACKGROUND

Wearable electronic devices are being used more and more for biological signal measurements. Optical measurement of biological signals is prone to errors from light reflecting from users' skin instead of traveling through the skin. Since most measurements are performed automatically and not under supervision, ensuring the reliability of measurements is particularly important. Some devices include dedicated sensors for detecting a proximity of the device to a user. However, these dedicated sensors consume precious space and power, often requiring sacrifices in either device design or performance.

SUMMARY

Embodiments of the systems, devices, methods, and apparatuses described in the present disclosure are directed to determining whether electronic devices are in a sensing state to measure physiological parameters. More particularly, the described embodiments relate to methods and systems for detecting and analyzing one or more sensing signals corresponding to light detected by the device to determine whether the device is in a sensing state, and using the sensing signals to determine physiological parameters if the device is in the sensing state.

One embodiment may take the form of a wearable electronic device that includes a device housing defining a rear surface, an optical sensing assembly, and a processing unit. The optical sensing assembly may include a light emitter adapted to emit light toward a user and a light detector adapted to detect light that has interacted with the user and output a sensing signal corresponding to the detected light. The processing unit may be operably coupled to the optical sensing assembly. The processing unit may be adapted to determine at least partially based on the sensing signal, whether the wearable electronic device is in a sensing state in which a separation distance from the rear surface to the user is less than or equal to a maximum sensing distance, and in response to determining that the wearable electronic device is in the sensing state, determine, based at least partially on the sensing signal, a physiological parameter of the user.

Another embodiment may take the form of a method that includes the steps of detecting, by an optical sensing assembly of a wearable electronic device, light that has interacted with a user, outputting a sensing signal corresponding to the detected light, determining, at least partially based on the sensing signal, whether the wearable electronic device is in a sensing state in which the rear surface is contacting the user, and in response to determining that the wearable electronic device is in the sensing state, determining a physiological parameter of the user based at least partially on the sensing signal.

Another embodiment may take the form of a method that includes the steps of performing an optical measurement including emitting light toward the user, detecting light that has interacted with the user, and determining, based on the detected light, whether a separation distance between the wearable electronic device and the user is less than or equal to a maximum sensing distance. The method further includes, in response to determining that the separation distance is less than or equal to the maximum sensing distance, determining, based at least partially on the detected light, at least one of a heart rate, blood-oxygen saturation value, or a total hemoglobin value. The method further includes, in response to determining that the separation distance is greater than the maximum sensing distance, repeating the optical measurement.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
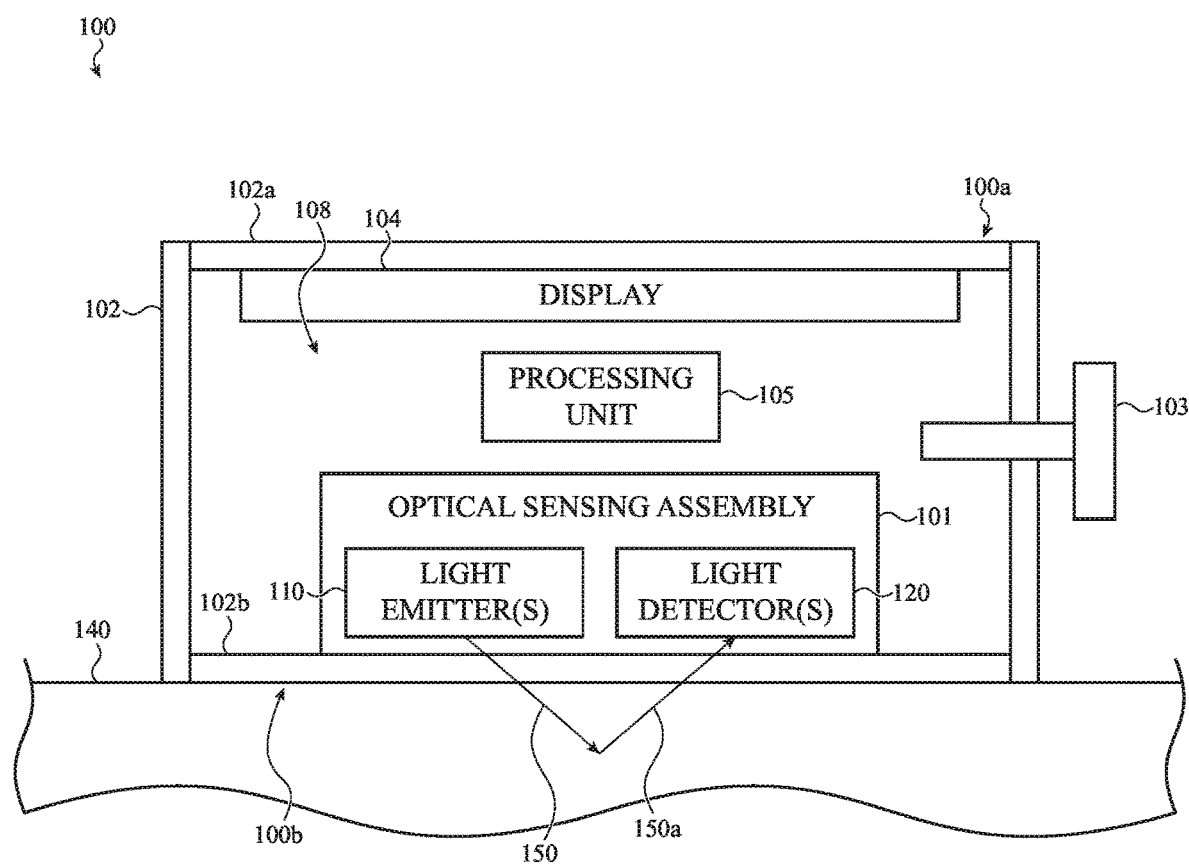
FIGS. 1A-1C are functional block diagrams of an example wearable electronic device that may be used to measure physiological parameters in a sensing state.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to determining one or more physiological parameters using a wearable electronic device. A wearable electronic device (e.g., an electronic watch) may detect and analyze one or more sensing signals corresponding to light detected by the device to determine whether the device is in a sensing state (e.g., the device is within a maximum sensing distance of a user). If the wearable electronic device is in the sensing state, the device may determine one or more physiological parameters from the same signals used to determine whether the device is in the sensing state. Using the same light emitters, light detectors, and sensing signals to determine whether the device is in a sensing state and to determine physiological parameters improves device performance by consuming less power and increases manufacturing efficiency and reduces device size by requiring fewer device components.

As used herein, the term "maximum sensing distance" may refer to the distance between the wearable electronic device and a user that is required for a reliable measurement of one or more physiological parameters. For many physiological parameters, reliable measurement requires that substantially all or a significant portion of the light emitted by light emitter(s) of the device travels through the user's skin before it is returned and sensed by light detector(s) of the device. When a light emitter of a wearable electronic device is within a maximum sensing distance of the user, substantially all or a significant portion of the light emitted by the light emitter travels through the user's skin before it is returned and sensed by the light detector(s) of the device. As a result, reliable measurements may be taken. In contrast, when a light emitter is not within the maximum sensing distance of the user, substantially all or a significant portion of the light emitted by the light emitter is reflected back to the light detector(s) without traveling through the user's skin. Accordingly, it is more difficult or impossible to take reliable measurements.

As noted above, the wearable electronic devices herein may detect and analyze one or more signals corresponding to light detected by the device to determine whether the device is within a maximum sensing distance of the user (e.g., whether a separation distance between the device and the user is less than or equal to the maximum sensing distance). At certain wavelengths, the light traveling through the user's skin in is significantly attenuated compared to the light that is reflected from the skin. As a result, the device may determine whether it is within the maximum sensing distance of the user based on a signal level (e.g., an amplitude, intensity, signal strength, etc.) of the detected signal. For example, in some cases, the device may determine that it is within the maximum sensing distance of the user if the signal level is below a predetermined threshold.

In some cases, determining that the device is in the sensing state includes determining that multiple locations or regions of the exterior surface of the device (e.g., a rear exterior surface of the device) are within the maximum sensing distance of the user. The wearable electronic device may include multiple light emitters and/or light detectors positioned at different locations beneath an exterior surface of the device. As a result, multiple light emitters and/or light detectors may be used to generate multiple sensing signals that may be analyzed to determine whether multiple different locations or regions of the exterior surface of the device are within the maximum sensing distance of the user. This may provide more reliable physiological measurements by ensuring that the device is not tilted or otherwise in a position in which emitted light does not sufficiently propagate through the user's skin.

Additionally or alternatively, determining that the device is in the sensing state may include emitting and detecting light at multiple different wavelengths. The wearable electronic device may analyze multiple sensing signals corresponding to each of the different wavelengths to achieve a more reliable determination that one or more locations or regions of the exterior surface of the device are within the maximum sensing distance of the user. For example, in some cases, the device may determine that it is within the maximum sensing distance of the user if the signal levels of multiple sensing signals satisfy a boundary condition. This may avoid or reduce false positives from single sensing signals.

As used herein, the term "light emitter" may refer to a spatially located source of light. A light emitter may include one or more light sources, including light-emitting diodes (LEDs), laser diodes, and the like. A light emitter may emit light in response to a signal, such as a control signal from a measurement engine or a processing unit or a current applied to the light emitter. In some cases, the wavelength of light emitted by a light emitter is not controllable, and the light emitter is used to emit light at a particular wavelength. Alternatively, the wavelength of light emitted by a light emitter may be controllable As used herein, the term "wavelength" may refer to a single wavelength value or a relatively narrow range of wavelengths (e.g., a 2 nm, 5 nm, or 15 nm range) in which the light has substantially the same optical properties, such as color.

The term "physically coupled," as used herein, may refer to two or more elements, structures, objects, components, parts or the like that are physically attached to one another. As used herein, "operably coupled" or "electrically coupled" may refer to two or more devices that operate with one another, communicate with one another, are in electrical connection with one another, and/or otherwise interact with one another in any suitable manner for operation and/or communication, including wired, wirelessly, or some combination thereof.

These and other embodiments are discussed with reference to FIGS. 1A-7. However, those skilled in the art will readily appreciate that the detailed description given herein with respect to these figures is for explanatory purposes only and should not be construed as limiting.

Figure 1B:
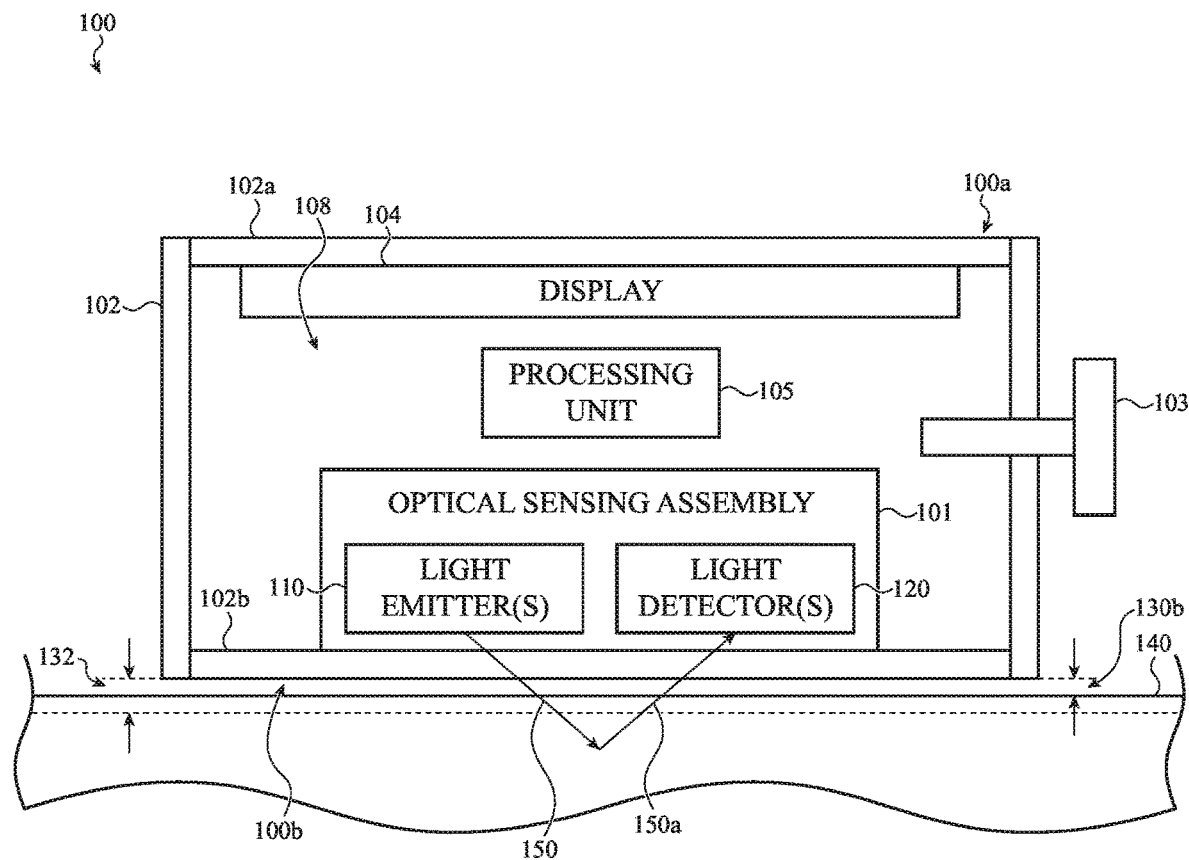
Figure 1C:
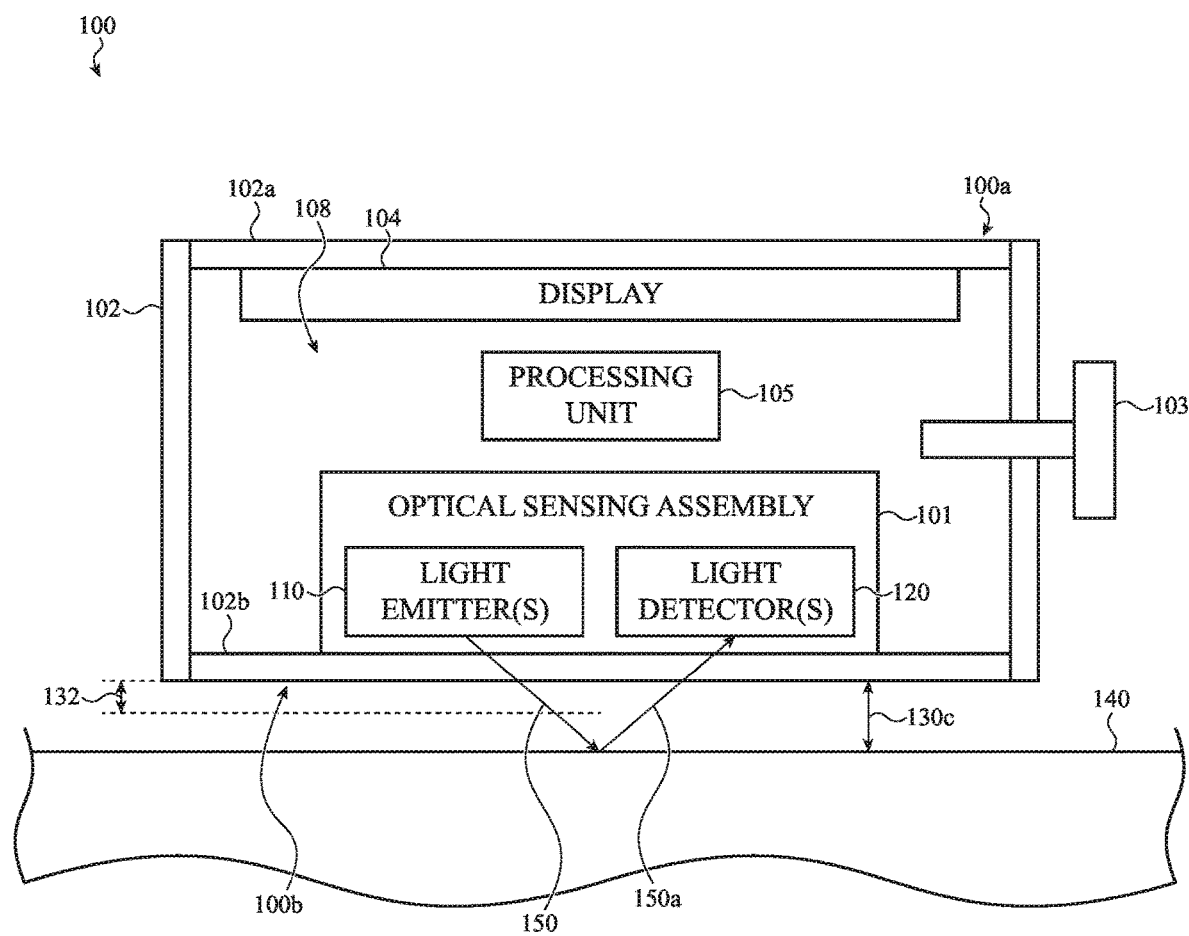

FIGS. 1A-1C are functional block diagrams of an example wearable electronic device 100 that may be used to measure physiological parameters in a sensing state. The wearable electronic device 100 may include an optical sensing assembly 101, which includes one or more light emitters 110 and one or more light detectors 120. The wearable electronic device 100 may further include a processing unit 105 for determining whether the wearable electronic device is in a sensing state and performing physiological measurements.

The wearable electronic device 100 may further include one or more input devices (e.g., a crown 103, a button, etc.), one or more output devices (e.g., a display 104, a speaker, etc.), and a processing unit 105. The wearable electronic device 100 may include an enclosure 102 that defines an interior volume 108. The input device(s), the output device(s), the processing unit 105, the measurement engine 106, and the optical sensing assembly 101 may be positioned at least partially within the interior volume 108 of the enclosure 102.

Broadly, the light emitters 110 emit light and the light detectors 120 detect light. The processing unit 105 analyzes one or more sensing signals corresponding to the detected light to determine whether the wearable electronic device 100 is in a sensing state, and if so, determines one or more physiological parameters from the sensing signals. As noted above, the wearable electronic device 100 may be in a sensing state when one or more locations or regions of an exterior surface of the wearable electronic device (e.g., a rear exterior surface 100b of the wearable electronic device) are within a maximum sensing distance of the user (e.g., whether a separation distance between the device and the user is less than or equal to the maximum sensing distance). As used herein, the term "maximum sensing distance" may refer to the distance between the wearable electronic device and a user that is required for a reliable measurement of one or more physiological parameters.

The maximum sensing distance may vary for different wearable electronic devices, users, and/or physiological parameters being detected. In some cases, the maximum sensing distance is zero (e.g., the device must be contacting the user to perform a reliable measurement). In some cases, the maximum sensing distance may be 0.1 mm, 0.5 mm, 1 mm, 2 mm, or more. The maximum sensing distance may be determined based on an amount that the wearable electronic device moves relative to the user during normal use. For example, the maximum sensing distance may be equal to or slightly greater than (e.g., within 5%, 10%, 25%, or 50%) of an amount the distance between the wearable electronic device and the user changes during normal use.

FIG. 1A illustrates the wearable electronic device 100 in a sensing state in which the rear exterior surface 100b is contacting the user 140 (e.g., the distance between the rear exterior surface 100b and the user 140 is zero). FIG. 1B illustrates the wearable electronic device 100 in a sensing state in which a separation distance 130b between the rear exterior surface 100b and the user 140 is less than or equal to a maximum sensing distance 132. In the examples shown in FIGS. 1A and 1B, the wearable electronic device 100 is close enough to the user 140 that substantially all or a significant portion of the light 150 emitted by the light emitter 110 travels through the user's skin before it is returned and sensed by light detector 120. As a result, in the sensing state, more reliable physiological measurements may be performed using the light emitter 110 and the light detector 120.

FIG. 1C illustrates the wearable electronic device 100 in a non-sensing state (e.g., not in a sensing state), because a separation distance 130c between the rear exterior surface 100b and the user 140 is greater than a maximum sensing distance 132. In the example shown in FIG. 1C, substantially all or a significant portion of the light 150 emitted by the light emitter 110 is reflected back to the light detector 120 without traveling through the user's skin. As a result, physiological measurements performed in the non-sensing state may be unreliable or less reliable than measurements performed in the sensing state.

Figure 2:
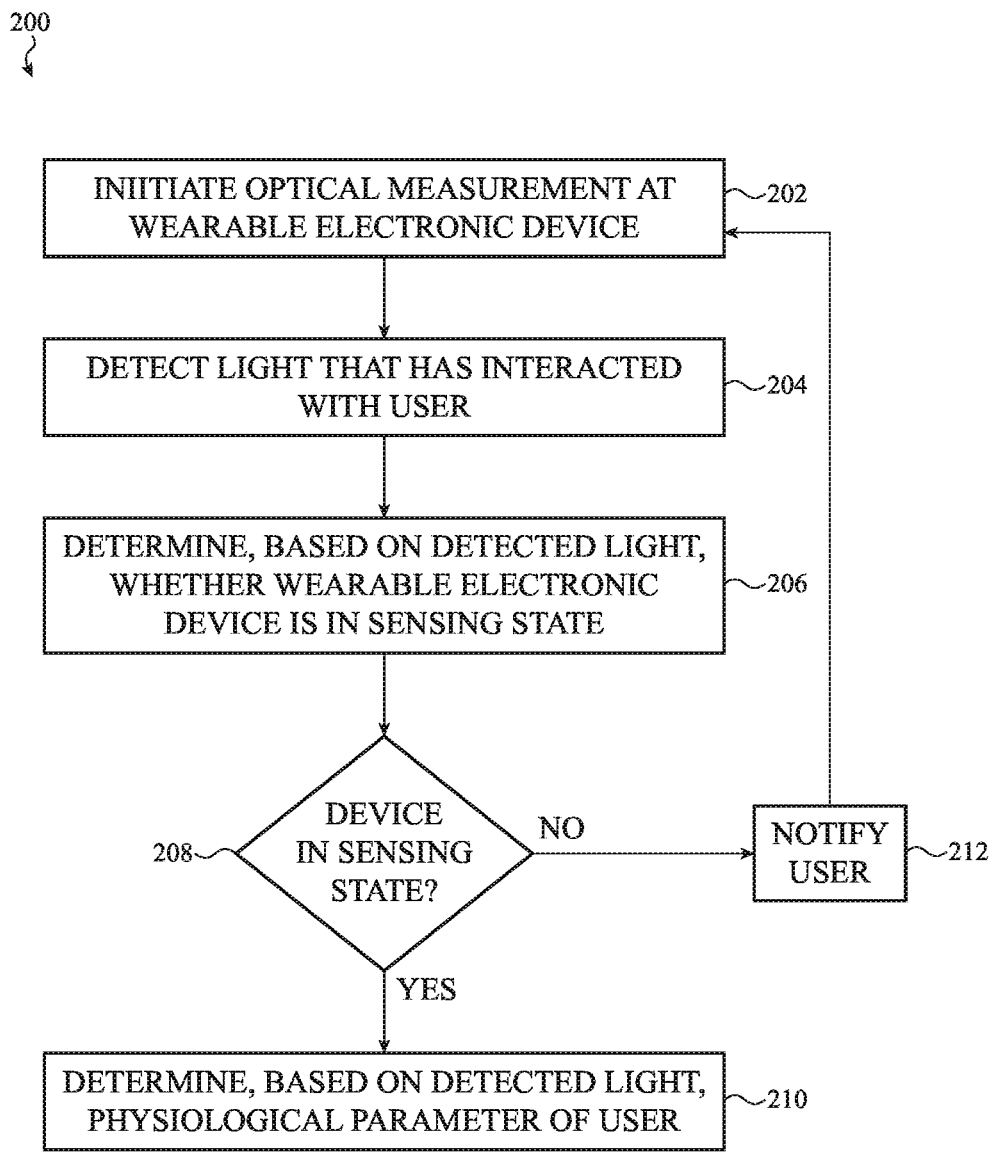
FIG. 2 is a flowchart depicting example operations of a method for determining if a wearable electronic device is in a sensing state.

As noted herein, the processing unit 105 may analyze sensing signal(s) received from the light detector(s) 120 to determine whether the wearable electronic device 100 is in a sensing state. The processing unit may determine whether it is within the maximum sensing distance of the user based on a signal level (e.g., an amplitude, intensity, signal strength, etc.) of the detected signal. For example, in some cases, the device may determine that it is within the maximum sensing distance of the user if the signal level is below a predetermined threshold. FIG. 2 is a flowchart depicting example operations of a method 200 for determining if a wearable electronic device is in a sensing state. The method 200 can be performed in whole or in part by one or more hardware resources of a wearable electronic device (e.g., wearable electronic device 100).

At operation 202, a processing unit (e.g., processing unit 105) initiates an optical measurement at a wearable electronic device. In an example optical measurement, one or more light emitters (e.g., light emitter(s) 110) emit light (e.g., light 150) toward a user (e.g., a user 140). The light interacts with the user, which may include a portion of the light being absorbed by the user's tissue (e.g., skin, blood vessels, muscles, and the like) and/or a portion of the light being returned (e.g., reflected, scattered, etc.) from the user.

At operation 204, the wearable electronic device (e.g., one or more light detectors 120) detects the light that has interacted with the user. As a result of the light interacting with the user, a returned portion (e.g., a returned portion 150a) of the light travels from the user to the wearable electronic device, where it is detected by the light detector. The light detector may output a sensing signal to the processing unit in response to detecting the returned portion of the light. The sensing signal may represent a waveform of the returned portion of the light.

The light detector(s) may be capable of outputting multiple signals, each corresponding to light emitted by a different light emitter. In some cases, the processing unit uses a multiplexing technique in which emission and/or sensing of the light from each light emitter occurs at different times. In some cases, the processing unit may cause the light detector(s) sense light from multiple emitters at the same time and use signal processing techniques to separate the signals or otherwise extract relevant information. In some cases, the optical sensing assembly 101 may include one or more physical components that allow the light detector(s) 120 to sense light from multiple emitters, including filters and the like.

At operation 206, the wearable electronic device (e.g., the processing unit 105) determines, based on the detected light, whether the wearable electronic device is in a sensing state. In various embodiments, a signal level (e.g., an amplitude, a power, or an intensity) of the sensing signal may correspond to a separation distance between the wearable electronic device and the user. The wearable electronic device may determine that it is in the sensing state by determining that it is within a maximum separation distance of the user (e.g., determining that a separation distance between the wearable electronic device and the user is less than or equal to the maximum sensing distance).

Figure 3:
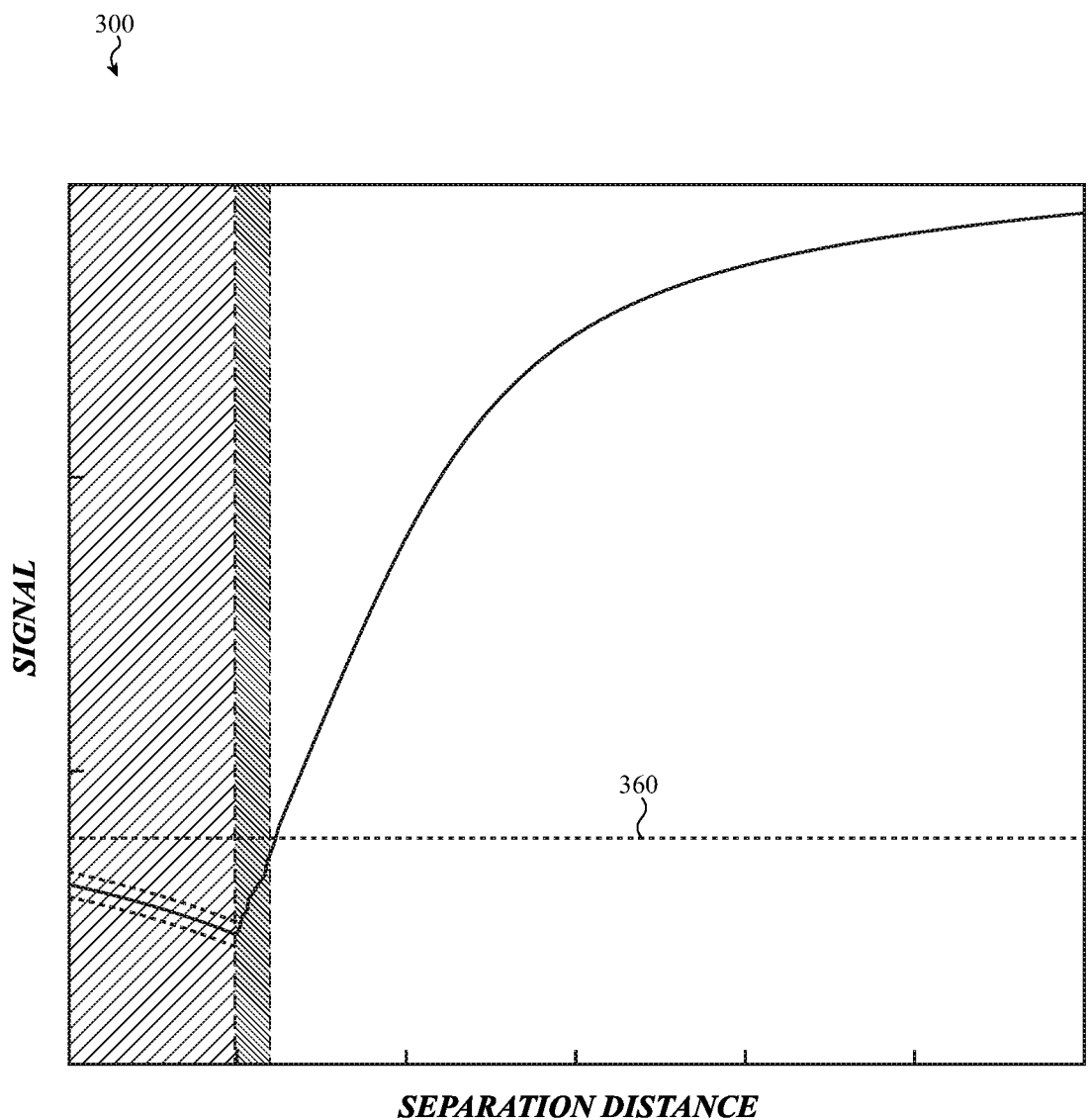
FIG. 3 illustrates a chart of an example relationship between signal level and separation distance.

FIG. 3 illustrates a chart 300 of an example relationship between signal level and separation distance. As shown in the chart 300, the signal level for greater separation distances is generally higher than the signal level for smaller separation distances. The wearable electronic device may determine whether the separation distance between the wearable electronic device and the user is less than or equal to the maximum separation distance Z by determining whether the signal level is below a predetermined threshold 360. As noted herein, when the wearable electronic device is within the maximum sensing distance Z of the user, substantially all or a significant portion of the light emitted by the light emitter(s) travels through the user's skin before it is returned and sensed by the light detector(s) of the device. In contrast, when a light emitter is not within the maximum sensing distance of the user, substantially all or a significant portion of the light emitted by the light emitter(s) is reflected back to the light detector(s) without traveling through the user's skin. In various embodiments, the light traveling through the user's skin in is significantly attenuated compared to the light that is reflected from the skin. For example, a significant portion of the light may be absorbed or otherwise not returned to the light detector. As a result, the signal level of the detected light is less for light that has traveled through the user's skin, and the wearable electronic device may determine whether it is within the maximum sensing distance of the user based on the signal level of the detected signal.

The maximum sensing distance Z may vary for different wearable electronic devices, users, and/or physiological parameters being detected. In some cases, the maximum sensing distance is zero (e.g., the device must be contacting the user to perform a reliable measurement). In some cases, the maximum sensing distance may be 0.1 mm, 0.5 mm, 1 mm, 2 mm, or more. The maximum sensing distance may be determined based on an amount that the wearable electronic device moves relative to the user during normal use. For example, the maximum sensing distance may be equal to or slightly greater than (e.g., within 5%, 10%, 25%, or 50%) of an amount the distance between the wearable electronic device and the user changes during normal use.

As noted herein, determining that the wearable electronic device is in the sensing state includes determining that multiple locations or regions of the exterior surface of the device (e.g., a rear exterior surface of the device) are within the maximum sensing distance of the user. The wearable electronic device may include multiple light emitters and/or light detectors positioned at different locations beneath an exterior surface of the device. As a result, multiple light emitters and/or light detectors may be used to generate multiple sensing signals that may be analyzed to determine whether multiple different locations or regions of the exterior surface of the device are within the maximum sensing distance of the user. This may provide more reliable physiological measurements by ensuring that the device is not tilted or otherwise in a position in which emitted light does not sufficiently propagate through the user's skin.

Additionally or alternatively, determining that the device is in the sensing state may include emitting and detecting light at multiple different wavelengths. The wearable electronic device may analyze multiple sensing signals corresponding to each of the different wavelengths to achieve a more reliable determination that one or more locations or regions of the exterior surface of the device are within the maximum sensing distance of the user. For example, in some cases, the device may determine that it is within the maximum sensing distance of the user if the signal levels of multiple sensing signals satisfy a boundary condition. This may avoid or reduce false positives from single sensing signals.

At operation 208, if the wearable electronic device is in the sensing state, the method 200 proceeds to operation 210. If the wearable electronic device is not in the sensing state, the method 200 proceeds to operation 212. In some cases, operation 212 is optional, and the method 200 may return to operation 202 if the wearable electronic device is not in the sensing state.

At operation 210, the processing unit determines, based on the detected light, at least one physiological parameter of the user. The processing unit may analyze the light detected during operation 204 (the same light that is used to determine whether the wearable electronic device is in the sensing state) to determine the physiological parameter(s). In some cases, the light emitter(s) emit additional light and/or the light detector(s) detect additional light for use in determining the physiological parameter(s). Example physiological parameters include, but are not limited to, a heart rate, a blood-oxygen saturation value, a blood glucose value, a total hemoglobin value, or the like. As noted herein, the detected light may originate from multiple light emitters and/or be emitted at multiple different wavelengths. In some cases the processing unit may analyze detected light from multiple emitters and/or detectors to determine the physiological parameter(s). In some cases, some or all of operation 210 may be performed by a device that is operably coupled to the wearable electronic device, such as a connected smartphone, a server, or another connected computing device.

At operation 212, the wearable electronic device notifies the user that the device is not in the sensing state. The notification may be provided in a graphical user interface of the wearable electronic device or another device that is operably coupled to the wearable electronic device (e.g., a smartphone). Additionally or alternatively, the wearable electronic device may take other actions besides notifying the user, including tightening a band of the wearable electronic device, adjusting a position of the wearable electronic device, changing an operating state of the wearable electronic device, or the like. Following operation 212 (or if operation 212 is omitted, following operation 208), the method 200 may return to operation 202 to initiate a subsequent optical measurement. In some cases, the wearable electronic device may wait a time period before initiating the subsequent optical measurement.

Figure 4:
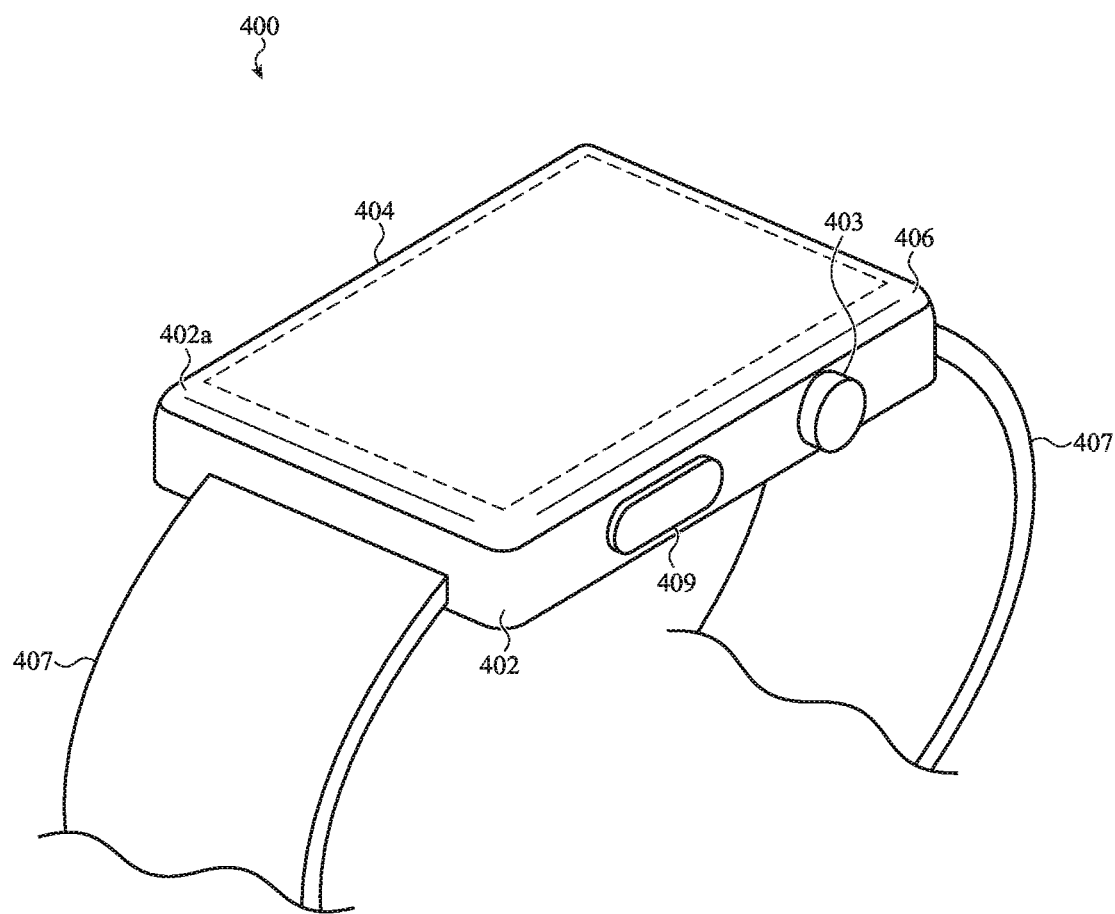
FIG. 4 illustrates an example watch that may incorporate an optical sensing assembly as described herein.

FIG. 4 illustrates an example watch 400 (e.g., an electronic watch or smart watch) that may incorporate an optical sensing assembly as described herein. The watch 400 may include a watch body 406 and a watch band 407. Other devices that may incorporate an optical sensing assembly include other wearable electronic devices, other timekeeping devices, other health monitoring or fitness devices, other portable computing devices, mobile phones (including smart phones), tablet computing devices, digital media players, or the like. The watch 400 may have similar components, structure, and/or functionality as the wearable electronic device 100 described with respect to FIGS. 1A-1C. The watch 400 may provide time and timing functions, receive messages and alerts, and may track activity of a user. In some cases, the watch may monitor biological conditions or characteristics (e.g., physiological parameters) of a user.

The watch body 406 may include an enclosure 402. The enclosure 402 may include a front side enclosure member that faces away from a user's skin when the watch 400 is worn by a user, and a back-side enclosure member that faces toward the user's skin. Alternatively, the enclosure 402 may include a singular enclosure member, or more than two enclosure members. The one or more enclosure members may be metallic, plastic, ceramic, glass, or other types of enclosure members (or combinations of such materials).

The enclosure 402 may include a cover 402a mounted to a front side of the watch body 406 (i.e., facing away from a user's skin) and may protect a display 404 mounted within the enclosure 402. The display 404 may produce graphical output that may be viewable by a user through the cover 402a. In some cases, the cover 402a may be part of a display stack, which may include a touch sensing or force sensing capability. The display may be configured to depict a graphical output of the watch 400, and a user may interact with the graphical output (e.g., using a finger, stylus, or other pointer). As one example, the user may select (or otherwise interact with) a graphic, icon, or the like presented on the display by touching or pressing (e.g., providing touch input) on the cover 402a at the location of the graphic. As used herein, the term "cover" may be used to refer to any transparent, semi-transparent, or translucent surface made out of glass, a crystalline material (such as sapphire or zirconia), plastic, or the like. Thus, it should be appreciated that the term "cover," as used herein, encompasses amorphous solids as well as crystalline solids. The cover 402a may form a part of the enclosure 202. In some examples, the cover 402a may be a sapphire cover. The cover 402a may also be formed of glass, plastic, or other materials.

The watch body 406 may include at least one input device or selection device, such as a button, crown, scroll wheel, knob, dial, or the like, which input device may be operated by a user of the watch 400.

The watch 400 may include one or more input devices (e.g., a crown 403, a button 409, a scroll wheel, a knob, a dial, or the like). The input devices may be used to provide inputs to the watch 400. The crown 403 and/or button 409 may be positioned along a portion of the enclosure 402, for example along a sidewall of the enclosure as shown in FIG. 4. In some cases, the enclosure 402 defines an opening through which a portion of the crown 403 and/or the button 409 extends.

The crown 403 may be user-rotatable, and may be manipulated (e.g., rotated, pressed) by a user. The crown 403 and/or button 409 may be mechanically, electrically, magnetically, and/or optically coupled to components within the enclosure 402, as one example. A user's manipulation of the crown 403 and/or button 409 may be used, in turn, to manipulate or select various elements displayed on the display, to adjust a volume of a speaker, to turn the watch 400 on or off, and so on.

In some embodiments, the button 409, the crown 403, scroll wheel, knob, dial, or the like may be touch sensitive, conductive, and/or have a conductive surface, and a signal route may be provided between the conductive portion and a circuit within the watch body 406, such as a processing unit.

The enclosure 402 may include structures for attaching the watch band 407 to the watch body 406. In some cases, the structures may include elongate recesses or openings through which ends of the watch band 407 may be inserted and attached to the watch body 406. In other cases (not shown), the structures may include indents (e.g., dimples or depressions) in the enclosure 402, which indents may receive ends of spring pins that are attached to or threaded through ends of a watch band to attach the watch band to the watch body. The watch band 407 may be used to secure the watch 400 to a user, another device, a retaining mechanism, and so on. In some cases, the watch 400 includes one or more components (e.g., motors, shape-memory alloys, etc.) for automatically or mechanically changing a tightness of the watch band 407, for example, to change a separation distance between the watch 400 and the user.

In some examples, the watch 400 may lack any or all of the cover 402a, the display 404, the button 409, or the crown 403. For example, the watch 400 may include an audio input or output interface, a touch input interface, a force input or haptic output interface, or other input or output interface that does not require the display 204, the button 409, or the crown 403. The watch 400 may also include the aforementioned input or output interfaces in addition to the display 404, the button 409, or the crown 403. When the watch 400 lacks the display, the front side of the watch 400 may be covered by the cover 402a, or by a metallic or other type of enclosure member.

Figure 5A:
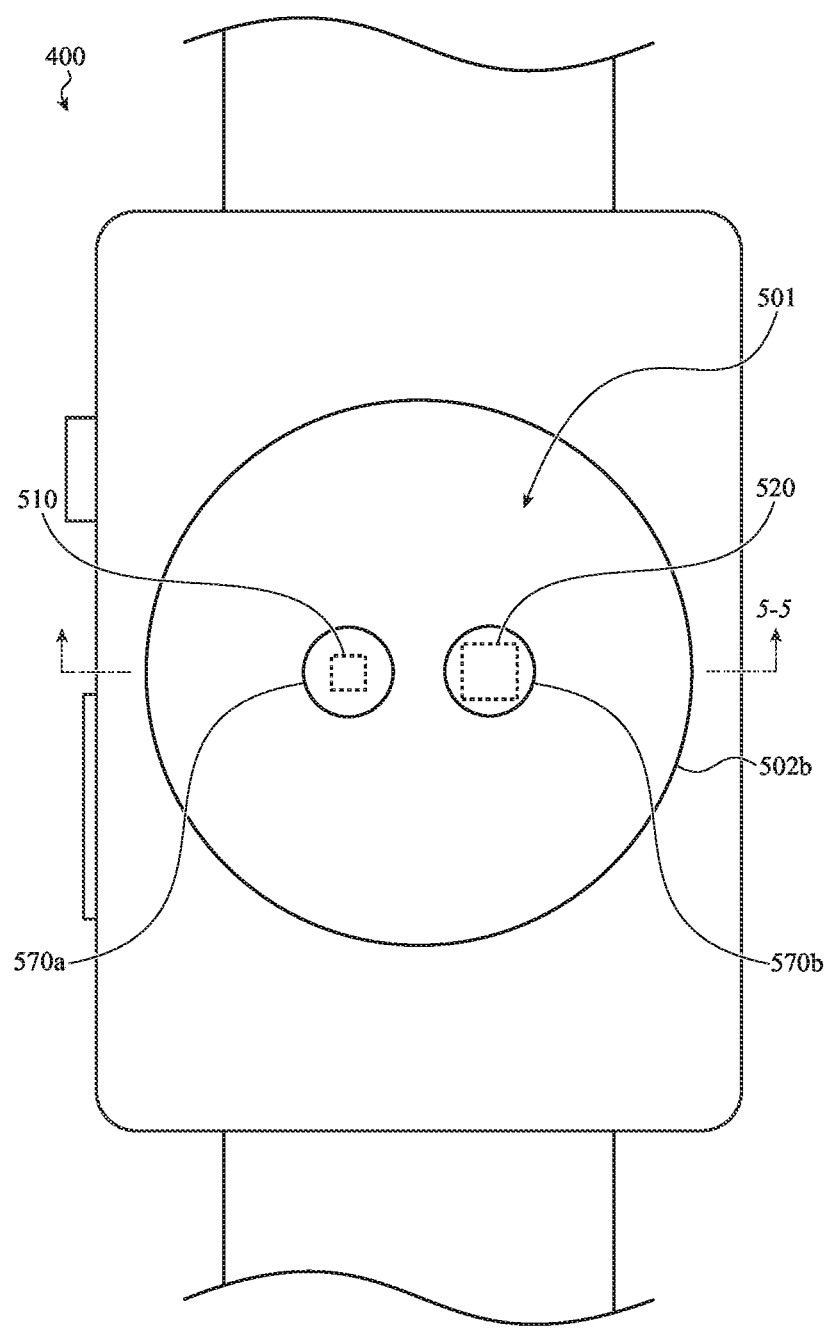
FIGS. 5A-5C illustrate a first embodiment of the example watch of FIG. 4, which includes a light emitter and a light detector beneath a rear exterior surface of the watch.
Figure 5B:
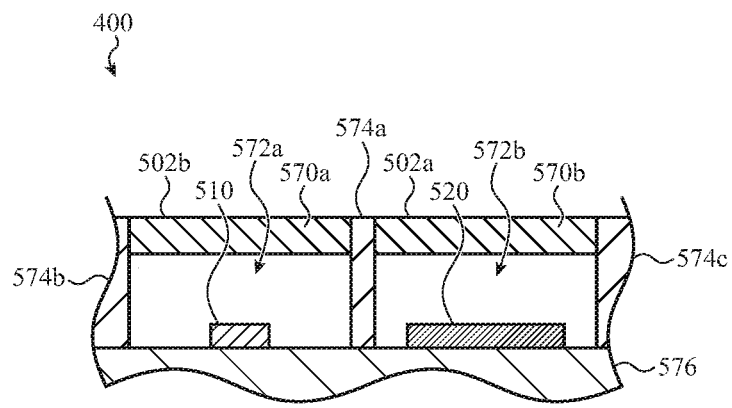
Figure 5C:
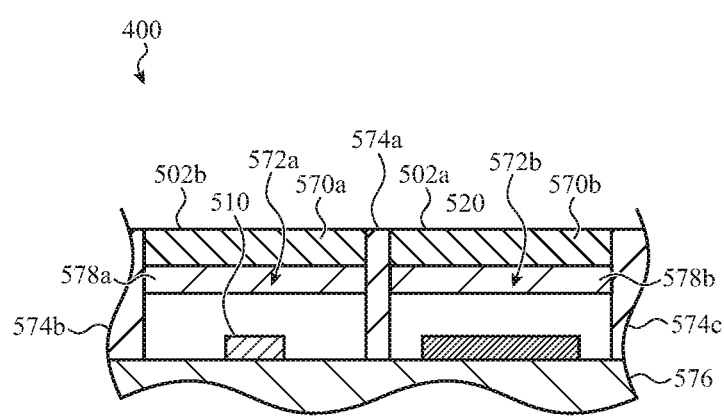

FIGS. 5A-5C illustrate a first embodiment of the example watch 400, which includes a light emitter and a light detector beneath a rear exterior surface of the watch. FIG. 5A illustrates a rear view of the first embodiment of the example watch 400. As shown in FIG. 5A, the watch 500 may include a rear cover 502b that defines a rear exterior surface of the watch. The cover 502b may define one or more windows through which the optical sensing assembly 501 may emit and/or detect light. For example, as shown in FIG. 5A, the cover 502b may define two windows 570a, 570b. A light emitter 510 of the optical sensing assembly 501 may emit light through the window 570a, and a light detector 520 of the optical sensing assembly may detect light through the window.

FIG. 5B illustrates a partial schematic cross-section view of the first embodiment of the example watch 400, taken through section line 5-5 of FIG. 5A. FIG. 5B illustrates the optical sensing assembly 501 positioned in an interior volume of the enclosure 402 and beneath the cover 502b. The cover 502b may be adapted to be positioned facing a user's skin (e.g., the user's wrist) while the watch 400 is worn. The light emitter 510 and light detector 520 may be used to determine if a separation distance between the cover 502b and the user is less than or equal to a maximum sensing distance to determine if the watch 400 is in a sensing state.

The optical sensing assembly 501 may include an optical sensing assembly housing 576. The optical sensing assembly housing 576 may define one or more cavities (e.g., cavities 572a, 572b) that are defined by one or more walls 574a, 574b, 574c (e.g., light blocking walls) of the optical sensing assembly housing. One or more of the walls (e.g., wall 574a) may separate the cavities 572a, 572b. One or more of the walls (e.g., walls 574b, 564c) may at least partially surround the light emitter 510 and/or the light detector 520. The optical sensing assembly 501 may be attached to an interior surface of the cover 502b. For example, the walls 574a-c may be attached to an interior surface of the cover 502b using adhesive or any other suitable mechanism for joining the optical sensing assembly housing 576 to the cover 502b. In some cases the walls 574a-c extend to an exterior surface of the cover 502b and define the windows 570a, 570b in the cover 502b. Additionally or alternatively, the windows 570a, 570b may be defined by masking or other treatments or techniques of the cover 502b.

In some cases, the optical sensing assembly 501 may include one or more optical elements (e.g., lenses, light films, and the like) for directing light emitted and/or detected by the optical sensing assembly. FIG. 5C shows the optical sensing assembly 501 with optical element 578a positioned between the light emitter 510 and the window 570a and optical element 578b positioned between the light detector 520 and the window 570b. In some cases, the cover 502b may have one or more electrodes thereon. The one or more electrodes on the cover 502b may be used to determine a biological parameter, such as a heart rate, an electrocardiogram, or the like. In some cases, the electrodes are used in combination with one or more additional electrodes, such as a surface of a crown assembly or other input device.

Figure 6A:
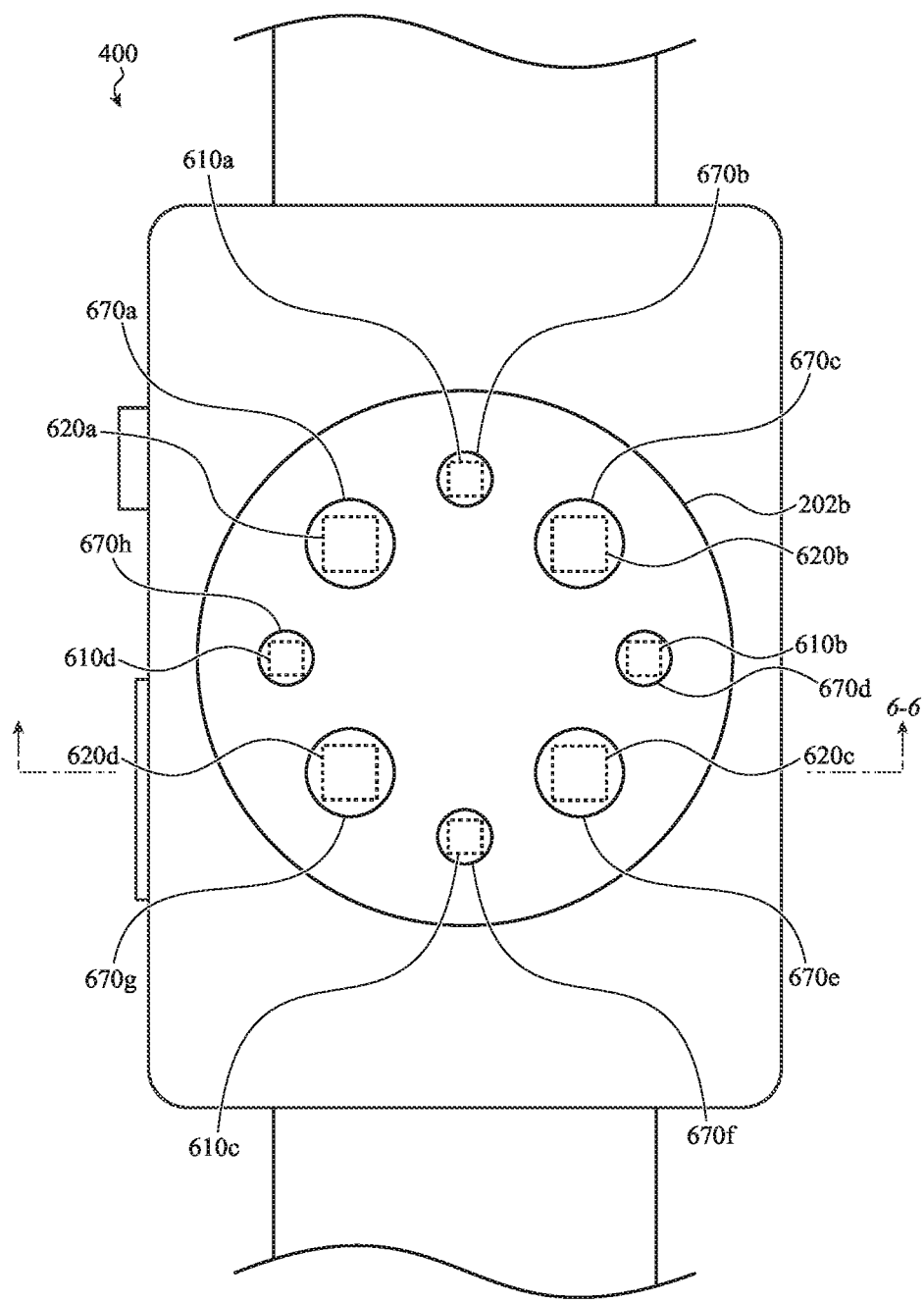
FIGS. 6A-6C illustrate a second embodiment of the example watch of FIG. 4, which includes an optical sensing assembly having multiple light emitters and light detectors beneath a rear exterior surface of the watch.
Figure 6B:
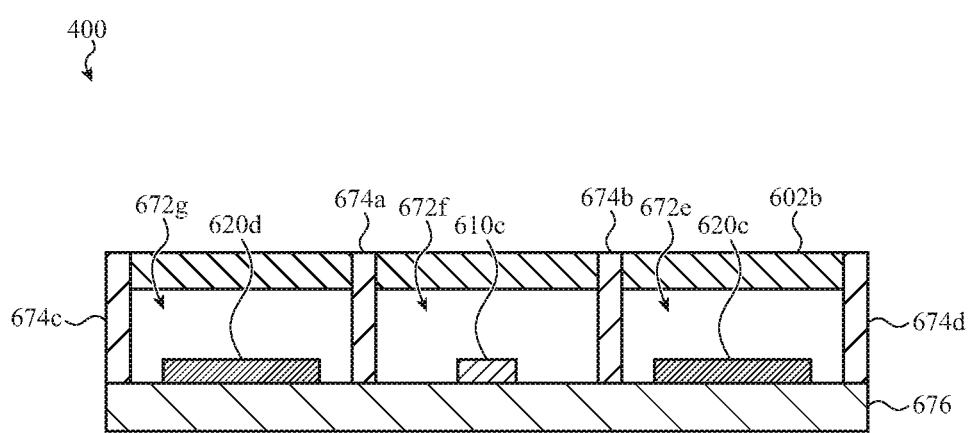
Figure 6C:
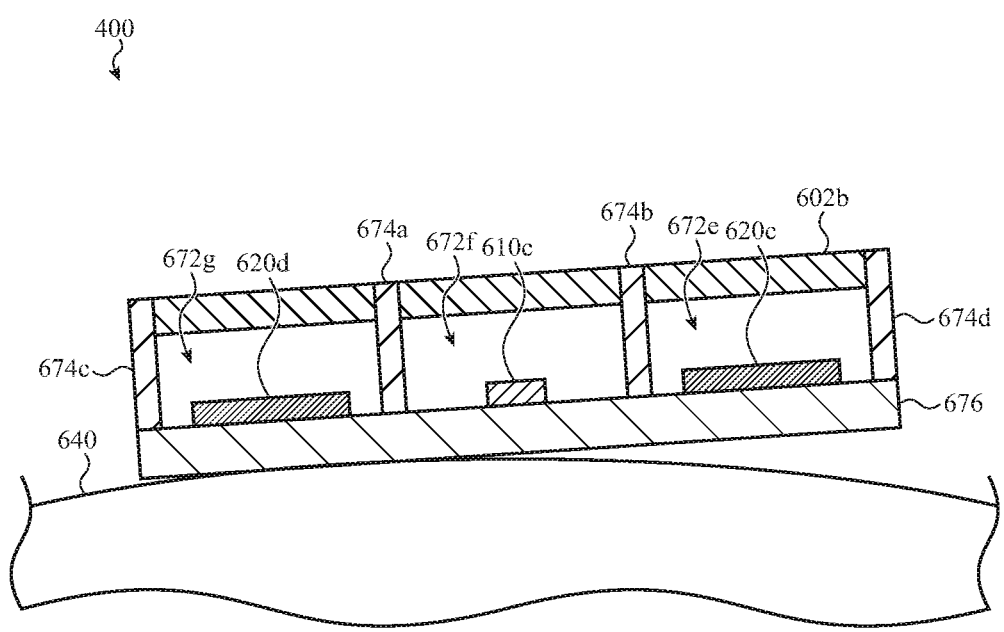

As noted herein, in some cases, the wearable electronic devices described herein may analyze multiple sensing signals to determine whether the device is in the sensing state. The wearable electronic devices may include multiple light emitters and/or light detectors positioned at different locations beneath an exterior surface of the device. FIGS. 6A-6C illustrate a second embodiment of the example watch 400, which includes an optical sensing assembly 601 having multiple light emitters 610a-d and light detectors 620a-d beneath a rear exterior surface of the watch. FIG. 6A illustrates a rear view of the second embodiment of the example watch 400.

The multiple light emitters 610a-d and/or light detectors 620a-d may be used to determine whether different locations or regions of the exterior surface of the watch 400 are within the maximum sensing distance of the user. This may provide more reliable physiological measurements by ensuring that the watch 400 is not tilted or otherwise in a position in which emitted light does not sufficiently propagate through the user's skin.

The second embodiment of the watch 400 may include similar components and/or functionality as other devices described herein. As shown in FIG. 6A, the watch 400 may include a rear cover 602b that defines a rear exterior surface of the watch. The cover 602b may define one or more windows through which the optical sensing assembly 601 may emit and/or detect light. For example, as shown in FIG. 6A, the cover 602b may define windows 670a-h through which one or more light emitters 610a-d emit light and/or one or more light detectors 620a-d detect light.

FIG. 6B illustrates a partial schematic cross-section view of the second embodiment of the example watch 400, taken through section line 6-6 of FIG. 6A. FIG. 6B illustrates the optical sensing assembly 601 positioned in an interior volume of the enclosure 402 and beneath the cover 602b. The cover 602b may be adapted to be positioned facing a user's skin (e.g., the user's wrist) while the watch 400 is worn. The light emitters 610a-d and light detectors 620a-d may be used to determine if a separation distance between the cover 602b and the user is less than or equal to a maximum sensing distance to determine if the watch 400 is in a sensing state.

The optical sensing assembly 601 may include an optical sensing assembly housing 676. The optical sensing assembly housing 676 may define one or more cavities (e.g., cavities 672e-g) beneath each window 672a-h that are defined by one or more walls (e.g., walls 674a-d) of the optical sensing assembly housing. In some cases, the optical sensing assembly 601 may include one or more optical elements (e.g., lenses, light films, and the like) for directing light emitted and/or detected by the optical sensing assembly.

In various embodiments, a light emitter 610a-d and a light detector 620a-d may define a sensor pair. The light emitter 610a-d of the sensor pair emits light that is detected by the light detector 620a-d of the sensor pair. The light emitters 610a-d and light detectors 620a-d may define multiple sensor pairs. A light emitter 610a-d may be a member of multiple sensor pairs in that the light emitted by the light emitter may be detected by multiple light detectors 620a-d. Similarly, a light detector 620a-d may be a member of multiple sensor pairs in that the light detector may detect light from multiple light emitters 610a-d. The respective light emitters 610a-d and/or light detectors 620a-d of each sensor pair may be positioned at different locations beneath an exterior surface of the watch 400. As a result, different sensor pairs may be used to determine whether different locations or regions of the exterior surface of the watch 400 are within the maximum sensing distance of the user. Similarly, different sensor pairs may provide different physiological data based on the different locations of the respective light emitters and light detectors of the sensor pairs, and the resulting different light paths between the respective light emitters and light detectors.

FIG. 6C illustrates an example situation in which multiple sensor pairs of the example watch 400 may be used to determine whether different locations or regions of the exterior surface of the watch 400 are within the maximum sensing distance of the user. The light emitter 610c may define a first sensor pair with the light detector 620c and a second sensor pair with the light detector 620d. Light emitted by the light emitter 610c may be detected by the light detectors 620c, 620d. Because the light detectors 620c, 620d are located at different positions beneath the rear exterior surface of the watch 400, each may be used to detect whether a region of the rear exterior surface is within a maximum sensing distance of a user 640. As shown in FIG. 6C, the light detected by the light detector 620d may indicate that the region of the rear exterior surface corresponding to the light detector 620d is within a maximum sensing distance of the user 640. Conversely, the light detected by the light detector 620c may indicate that the region of the rear exterior surface corresponding to the light detector 620c is not within a maximum sensing distance of the user 640. As a result, as shown in FIG. 6C, the watch is tilted, and may not be able to make reliable physiological measurements. The example of FIG. 6C shows only two sensor pairs, but the optical sensing assembly 601 may define up to 16 sensor pairs.

In some cases, determining that the watch 400 is in the sensing state includes determining that each sensor pair of the optical sensing assembly 601 indicates that the region of the rear exterior surface corresponding to the sensor pair is within the maximum sensing distance. Alternatively, determining that the watch 400 is in the sensing state may include determining that a majority or another threshold number of the sensor pairs of the optical sensing assembly 601 indicate that the region of the rear exterior surface corresponding to the sensor pair is within the maximum sensing distance. In some cases, the watch 400 may reject signals detected by sensor pairs that indicate the region of the watch is not within the maximum sensing distance and may use non-rejected signals to determine one or more physiological parameters. Alternatively, the watch 400 may not perform any determination of physiological parameters until all of the sensor pairs indicate that the regions corresponding to each sensor pair are within the maximum sensing distance of the user 640.

Additionally or alternatively, determining that the device is in the sensing state may include emitting and detecting light at multiple different wavelengths. For example, the light emitters 610a-d may include two or more light sources for emitting light at different wavelengths. One or more of the light detectors 620a-d may detect light from different light emitters 610a-d and/or having different wavelengths. The watch 400 may analyze multiple sensing signals corresponding to each of the different wavelengths to achieve a more reliable determination that one or more locations or regions of the exterior surface of the watch are within the maximum sensing distance of the user 640. For example, in some cases, the watch 400 may determine that it is within the maximum sensing distance of the user 640 if the signal levels of multiple sensing signals satisfy a boundary condition. This may avoid or reduce false positives from single sensing signals.

Figure 7:
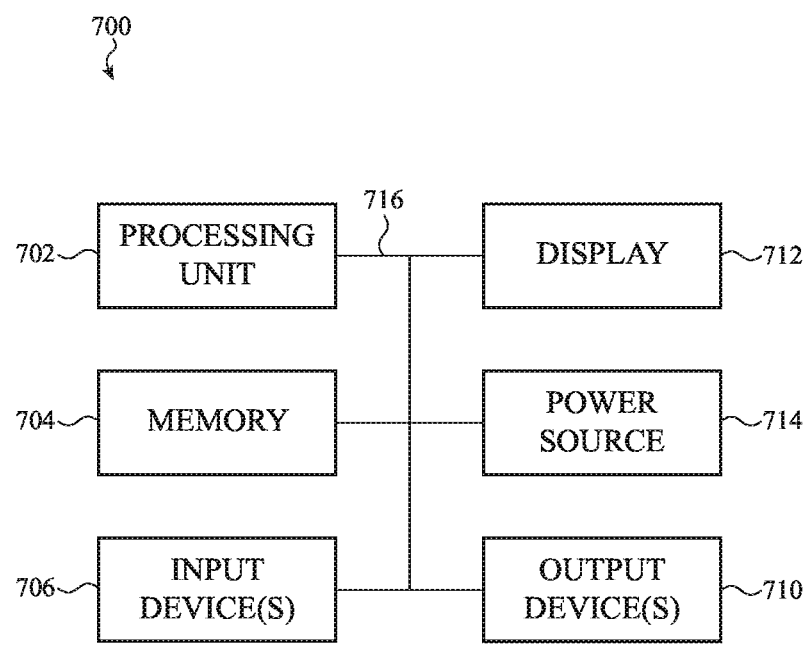
FIG. 7 illustrates a sample electrical block diagram of an electronic device that may incorporate an optical sensing assembly as described herein.

FIG. 7 illustrates a sample electrical block diagram of an electronic device 700 that may incorporate an optical sensing assembly as described herein. The electronic device may in some cases take the form of any of the electronic devices described with reference to FIGS. 1A-6B, or other portable or wearable electronic devices. The electronic device 700 can include one or more of a display 712, a processing unit 702, a power source 714, a memory 704 or storage device, input devices 706 (e.g., light sensor(s)), and output devices 710 (a light emitter(s)).

The processing unit 702 can control some or all of the operations of the electronic device 700. The processing unit 702 can communicate, either directly or indirectly, with some or all of the components of the electronic device 700. For example, a system bus or other communication mechanism 716 can provide communication between the processing unit 702, the power source 714, the memory 704, the input device(s) 706, and the output device(s) 710.

The processing unit 702 can be implemented as any electronic device capable of processing, receiving, or transmitting data or instructions. For example, the processing unit 702 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 700 can be controlled by multiple processing units. For example, select components of the electronic device 700 (e.g., an input device 706) may be controlled by a first processing unit and other components of the electronic device 700 (e.g., the display 712) may be controlled by a second processing unit, where the first and second processing units may or may not be in communication with each other. In some cases, the processing unit 702 may determine a biological parameter of a user of the electronic device, such as an ECG for the user.

The power source 714 can be implemented with any device capable of providing energy to the electronic device 700. For example, the power source 714 may be one or more batteries or rechargeable batteries. Additionally or alternatively, the power source 714 can be a power connector or power cord that connects the electronic device 700 to another power source, such as a wall outlet.

The memory 704 can store electronic data that can be used by the electronic device 700. For example, the memory 704 can store electrical data or content such as, for example, audio and video files, documents and applications, device settings and user preferences, timing signals, control signals, and data structures or databases. The memory 704 can be configured as any type of memory. By way of example only, the memory 704 can be implemented as random access memory, read-only memory, Flash memory, removable memory, other types of storage elements, or combinations of such devices.

In various embodiments, the display 712 provides a graphical output, for example associated with an operating system, user interface, and/or applications of the electronic device 700. In one embodiment, the display 712 includes one or more sensors and is configured as a touch-sensitive (e.g., single-touch, multi-touch) and/or force-sensitive display to receive inputs from a user. For example, the display 712 may be integrated with a touch sensor (e.g., a capacitive touch sensor) and/or a force sensor to provide a touch- and/or force-sensitive display. The display 712 is operably coupled to the processing unit 702 of the electronic device 700.

The display 712 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 712 is positioned beneath and viewable through a cover that forms at least a portion of an enclosure of the electronic device 700. In various embodiments, graphical outputs of the display 712 may be responsive to estimated physiological parameters determined by the device 700. For the processing unit 702 may cause the display 712 to display a notification or other graphical object(s) related to physiological parameters.

In various embodiments, the input devices 706 may include any suitable components for detecting inputs. Examples of input devices 706 include light sensors, temperature sensors, audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 706 may be configured to detect one or more particular types of input and provide a signal (e.g., an input signal) corresponding to the detected input. The signal may be provided, for example, to the processing unit 702.

As discussed above, in some cases, the input device(s) 706 include a touch sensor (e.g., a capacitive touch sensor) integrated with the display 712 to provide a touch-sensitive display. Similarly, in some cases, the input device(s) 706 include a force sensor (e.g., a capacitive force sensor) integrated with the display 712 to provide a force-sensitive display.

The output devices 710 may include any suitable components for providing outputs. Examples of output devices 710 include light emitters, audio output devices (e.g., speakers), visual output devices (e.g., lights or displays), tactile output devices (e.g., haptic output devices), communication devices (e.g., wired or wireless communication devices), and so on, or some combination thereof. Each output device 710 may be configured to receive one or more signals (e.g., an output signal provided by the processing unit 702) and provide an output corresponding to the signal.

In some cases, input devices 706 and output devices 710 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 702 may be operably coupled to the input devices 706 and the output devices 710. The processing unit 702 may be adapted to exchange signals with the input devices 706 and the output devices 710. For example, the processing unit 702 may receive an input signal from an input device 706 that corresponds to an input detected by the input device 706. The processing unit 702 may interpret the received input signal to determine whether to provide and/or change one or more outputs in response to the input signal. The processing unit 702 may then send an output signal to one or more of the output devices 710, to provide and/or change outputs as appropriate.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

As described above, one aspect of the present technology is determining physiological parameters, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

What is claimed is:

1. A wearable electronic device comprising:
  a device housing defining a rear surface;
  an optical sensing assembly comprising:
    a light emitter adapted to emit light toward a user; and
    a set of light detectors, each light detector of the set of light detectors adapted to:
      detect light that has interacted with the user;
      output a first sensing signal corresponding to the detected light at a first light detector of the set of light detectors; and
      output a second sensing signal corresponding to the detected light at a second light detector of the set of light detectors;
  a processing unit operably coupled to the optical sensing assembly and adapted to:
    determine, at least partially based on the first sensing signal and the second sensing signal, whether the wearable electronic device is in a sensing state in which:
      a first separation distance from a first position along the rear surface to the user is less than or equal to a maximum sensing distance; and
      a second separation distance from a second position along the rear surface to the user is less than or equal to the maximum sensing distance; and
    in response to determining that the wearable electronic device is in the sensing state, determine a physiological parameter of the user based at least partially on at least one of the first sensing signal or the second sensing signal.

2. The wearable electronic device of claim 1, wherein:
  the light emitter is a first light emitter;
  the light that has interacted with the user comprises a returned portion of the light emitted by the first light emitter;
  the optical sensing assembly further comprises a second light emitter adapted to emit light toward the user;
  the set of light detectors is further adapted to:
    detect a returned portion of the light emitted by the second light emitter that has interacted with the user; and
    output a third sensing signal corresponding to the returned portion of the light emitted by the second light emitter; and
  the processing unit is adapted to determine whether the wearable electronic device is in the sensing state further based on the third sensing signal.

3. The wearable electronic device of claim 2, wherein the processing unit is adapted to determine the physiological parameter of the user further based on the third sensing signal.

4. The wearable electronic device of claim 1, wherein:
  the first light detector detects a first portion of the light emitted by the light emitter that has interacted with the user;
  the first sensing signal corresponds to the first portion of the light emitted by the light emitter;
  the second light detector detects a second portion of the light emitted by the light emitter that has interacted with the user;
  the second sensing signal corresponds to the second portion of the light emitted by the light emitter; and
  the processing unit determines the physiological parameter of the user based at least partially on the first sensing signal and the second sensing signal.

5. The wearable electronic device of claim 1, wherein determining that the wearable electronic device is in the sensing state comprises determining that a signal level of at least one of the first sensing signal or the second sensing signal is below a predetermined threshold.

6. The wearable electronic device of claim 5, wherein the signal level is one of an amplitude of the first sensing signal or the second sensing signal, a power of the first sensing signal or the second sensing signal, or an intensity of the first sensing signal or the second sensing signal.

7. The wearable electronic device of claim 1, wherein the physiological parameter is one of a heart rate, a blood-oxygen saturation value, or a total hemoglobin value.

8. The wearable electronic device of claim 1, wherein:
  the wearable electronic device further comprises a display operably coupled to the processing unit and adapted to provide a graphical output viewable along a front surface of the device housing opposite the rear surface; and
  the processing unit is further adapted to modify the graphical output of the display based on the determined physiological parameter.

9. A method comprising:
  detecting, by an optical sensing assembly of a wearable electronic device, light that has interacted with a user, the optical sensing assembly comprising a first light detector and a second light detector;

outputting a first sensing signal corresponding to light detected by the first light detector and a second sensing signal corresponding to light detected by the second light detector;
determining, at least partially based on the first sensing signal and the second sensing signal, whether the wearable electronic device is in a sensing state in which the first detector and the second detector are within a maximum sensing distance; and
in response to determining that the first detector and the second detector are within the maximum sensing distance, determining a physiological parameter of the user based at least partially on at least one of the first sensing signal or the second sensing signal.

10. The method of claim 9, wherein determining that the wearable electronic device is in the sensing state comprises determining that a signal level of at least one of the first sensing signal or the second sensing signal is below a predetermined threshold.

11. The method of claim 9, wherein:
the light that has interacted with the user is light emitted by a first light emitter of the optical sensing assembly;
the method further comprises:
detecting, by the optical sensing assembly, light emitted by a second light emitter of the optical sensing assembly that has interacted with the user;
outputting a third sensing signal corresponding to the detected light emitted by the second light emitter; and
determining whether the wearable electronic device is in the sensing state comprises determining whether the first sensing signal, the second sensing signal, or the third sensing indicate that the wearable electronic device is contacting the user.

12. The method of claim 11, wherein determining the physiological parameter of the user is further based on the third sensing signal.

13. The method of claim 11, wherein:
the method further comprises:
determining, using at least one of the first sensing signal or the second sensing signal, that a first portion of the wearable electronic device corresponding to the first light emitter is contacting the user;
determining, using the third sensing signal, that a second portion of the wearable electronic device corresponding to the second light emitter is not contacting the user; and
in response to determining that the first portion of the wearable electronic device is contacting the user and the second portion of the wearable electronic device is not contacting the user, determining the physiological parameter using at least one of the first sensing signal or the second sensing signal.

14. The method of claim 11, wherein:
the light emitted by the first light emitter has a first wavelength; and
the light emitted by the second light emitter has as second wavelength different from the first wavelength.

15. A method for determining whether a wearable electronic device is contacting a user, the method comprising:
performing an optical measurement, comprising:
emitting light toward the user;
detecting, using a set of light detectors comprising a first light detector and a second light detector, light that has interacted with the user; and
determining, based on a first sensing signal output by the first light detector and a second sensing signal output by the second light detector, whether a separation distance between the wearable electronic device and the user is less than or equal to a maximum sensing distance;
in response to determining that the separation distance is less than or equal to the maximum sensing distance, determining, based at least partially on at least one of the first sensing signal or the second sensing signal, at least one of a heart rate, blood-oxygen saturation value, or a total hemoglobin value; and
in response to determining that the separation distance is greater than the maximum sensing distance, repeating the optical measurement.

16. The method of claim 15, further comprising, in response to determining that the separation distance is greater than the maximum sensing distance, notifying the user.

17. The method of claim 15, further comprising, in response to determining that the separation distance is greater than the maximum sensing distance, tightening a watch band of the wearable electronic device.

18. The method of claim 15, wherein the light comprises light having a first wavelength and light having a second wavelength different from the first wavelength.

19. The method of claim 15, wherein emitting the light toward the user comprises using a light emitter separated from the first light detector by a first distance and the light emitter separated from the second light detector by a second distance.

20. The method of claim 15, wherein:
the separation distance is a first separation distance; and
the method further comprises determining, based on at least one of the first sensing signal or the second sensing signal, whether a second separation distance between the wearable electronic device and the user is less than or equal to the maximum sensing distance.

* * * * *